(12) United States Patent
Bologna

(10) Patent No.: US 6,699,172 B2
(45) Date of Patent: Mar. 2, 2004

(54) GENERATOR OF ELECTROMAGNETIC WAVES FOR MEDICAL USE

(76) Inventor: Marco Bologna, Via del Capitel, 2-37131 Verona (IT)

( * ) Notice: Subject to any disclaimer, the term of this patent is extended or adjusted under 35 U.S.C. 154(b) by 45 days.

(21) Appl. No.: 10/220,713

(22) PCT Filed: Mar. 1, 2001

(86) PCT No.: PCT/IT01/00099
§ 371 (c)(1),
(2), (4) Date: Sep. 3, 2002

(87) PCT Pub. No.: WO01/64284
PCT Pub. Date: Sep. 7, 2001

(65) Prior Publication Data
US 2003/0023129 A1 Jan. 30, 2003

(30) Foreign Application Priority Data
Mar. 3, 2000 (IT) .................... VR2000A0020
Jul. 21, 2000 (IT) .................... VR2000A0070

(51) Int. Cl.[7] ................................ A61N 1/00
(52) U.S. Cl. ............................................ 600/13
(58) Field of Search ......................... 600/9–15

(56) References Cited
U.S. PATENT DOCUMENTS

| | | |
|---|---|---|
| 4,889,526 A | 12/1989 | Rauscher et al. |
| 5,170,784 A | 12/1992 | Leon et al. |
| 5,480,373 A * | 1/1996 | Fischer et al. ............... 600/14 |
| 5,527,259 A | 6/1996 | Grace et al. |
| 5,562,597 A | 10/1996 | Van Dick |
| 6,004,257 A * | 12/1999 | Jacobson ..................... 600/9 |
| 6,425,851 B1 * | 7/2002 | Kiontke ........................ 600/9 |

FOREIGN PATENT DOCUMENTS

| | | |
|---|---|---|
| EP | 0 074 748 | 3/1983 |
| WO | WO 89 05673 | 6/1989 |

* cited by examiner

Primary Examiner—Samuel G. Gilbert
(74) Attorney, Agent, or Firm—Greenberg Traurig, LLP; Christopher Darrow, Esq.

(57) ABSTRACT

A generator (10) of electromagnetic waves for medical use for personal physical and psychological wellbeing, generating a succession of electromagnetic waves, at least one oscillating circuit (12; 15a–15g) to generate one or more wave harmonics from one or more oscillating waves at one or more fundamental pre-determined frequencies, as well as a control device for mixing the waves and an emitter (14) for emitting the waves into a room which can be occupied by one or more users; each wave generated by mixing of said waves is made up of the sum of a series of fifth, ninth, thirteenth, seventeenth, twenty first, twenty fifth and twenty ninth order harmonics with respect to a fundamental frequency.

10 Claims, 2 Drawing Sheets

GENERATOR OF ELECTROMAGNETIC WAVES FOR MEDICAL USE

TECHNICAL FIELD

The present invention relates to a generator of electromagnetic waves for medical use for personal physical and psychological wellbeing.

More specifically, this invention concerns an electromagnetic appliance able to generate an electromedical field to treat the body and achieve a high level of wellbeing.

BACKGROUND ART

It is well known that electromagnetic appliances are used in electromedical applications designed to offer a wide range of benefits for the human body.

These appliances may consist of electrodes to be applied to the skin of various parts of the body, electrically connected to extremely low energy sources and designed to send micro-discharges detectable to the muscles in the zone treated in order to stimulate dilation and contraction to relax and treat the tissues.

Applications of this type achieve results similar to or better than those obtained with acupuncture.

To date, use has also been made of electromagnetic appliances consisting of belts or straps electrically connected to special electrodes which in this case generate an electromagnetic field to treat muscle masses either partially damaged or with compromised elasticity.

The effects obtained from these applications can be compared to a massage and these devices are therefore particularly suitable both in the treatment of muscle masses and to give the user a sense of wellbeing.

Other devices consist of conductors in general which are applied to certain parts of the body and transmit energy fields by means of pulse trains generated by a suitable source.

Document U.S. Pat. No. 5,527,259 describes an apparatus for therapeutic treatment comprising:
  a generator unit adapted to provide alternating current;
  a control means in electrical connection with said generator unit and adapted to receive as input alternating current from the generator unit and to provide electrical signals as output; said electrical signals at a frequency in the range 0.5 to 25 Hz;
  and one applicator coils in electrical connection with said control means and adapted to convert the electrical signals to magnetic fields.

The magnetic field induction multi-pulse therapy device described in U.S. Pat. No. 5,527,259 works controlling the characteristics of signals applied to the applicator coils and with the possibility of setting the duration of treatment and the primary frequency of the applied magnetic field that can be applied. Moreover said device allows the selection of the duration of treatment and the frequency to be chosen as well as automatic programs suitable to performs cycles of pre-determined frequencies applications for a certain predetermined time.

One problem is represented by the fact that some of these devices may be beneficial in stimulating a certain muscle bundle, but damaging to the overall health of the body of the patient undergoing this type of treatment.

Another problem is represented by the fact that these types of appliance necessarily require electrodes to be applied to the skin.

These may be self-adhesive, in the form of belts or straps or whatever other means is used to transmit the electromagnetic waves.

A further problem is the fact that the individual electrodes must be correctly positioned in order to achieve the optimum result, namely resolution of the physical problem which the appliance is being used to treat.

Correct positioning of the electrodes undoubtedly favours resolution of the physical problems.

Incorrect positioning, on the other hand, may increase the pain and discomfort for the user.

There is also a problem associated with the space taken up by these appliances, as a result of their size and the need to connect electrodes requiring varying lengths of cable which may easily become tangled and are sometimes difficult to identify correctly.

This often requires the presence of an operator who must position the electrodes on the user's body, as well as supervising control and command of the appliance itself.

DESCRIPTION OF THE INVENTION

The present invention intends to provide a generator of electromagnetic waves for medical use able to eliminate or significantly reduce the above problems.

This invention also intends to provide a generator of electromagnetic waves for medical use which is easy to transport and simple to use.

A further aim of this invention is to provide a generator of electromagnetic waves for medical use which can be used by more than one person at a time.

An additional aim of this invention is to provide a generator of electromagnetic waves for medical use able to transmit successions of selected frequency wave forms without there being direct contact with the skin of the user or users.

Last but not least, this invention also intends to provide an electromagnetic wave generator for medical use which is reliable and safe in accordance with current legislation and standards on the emission of electromagnetic radiation for domestic appliances.

This is achieved by means of a generator of electromagnetic waves for medical use for personal physical and psychological wellbeing having the features described in the main claim.

The dependent claims describe advantageous embodiments of the invention.

According to the invention, the generator of electromagnetic waves for medical use for personal physical and psychological wellbeing comprises components for generating electromagnetic waves, components for mixing said waves and components for emitting these waves into a room which can be occupied by one or more users.

According to a particularly advantageous embodiment of this invention, the generator generates and emits wave forms equivalent to the sum of the fifth, ninth, thirteenth, seventeenth, twenty first, twenty fifth and twenty ninth order harmonics of a series of predetermined basic frequencies into the surrounding environment at an established power.

According to this invention, these wave forms are emitted into the environment surrounding the generator in succession according to pre-determined criteria and for pre-determined periods of time.

In particular, the length of time for which a given wave form derived from a given fundamental frequency is emitted may be different with respect to the period of emission of another wave form derived from another fundamental frequency.

In addition, the criteria determining the succession of wave forms to be emitted into the environment surrounding the generator may be established by means of appropriate means of command and control according to the beneficial effects to be obtained from said emissions.

In accordance with a feature of the invention, the means of control for the mixing of the waves consist of an adder circuit designed to simultaneously emit each fifth, ninth, thirteenth, seventeenth, twenty first, twenty fifth and twenty ninth harmonic of a pre-determined fundamental frequency in such a way as to obtain a sinusoidal wave form which is emitted into the environment for a pre-determined period of time.

Generation of these wave forms is subsequently repeated a number of times, but using different fundamental frequencies depending on the particular beneficial effects to be obtained. The final result to the user of the appliance according to the invention consists of the emission of a succession of different wave forms into the environment, each for a given period of time and predetermined power to form a sort of "music" which is diffused around the generator, with an effect on people located near the generator itself.

According to a feature of the invention, the fundamental frequencies from which the fifth, ninth, thirteenth, seventeenth, twenty first, twenty fifth and twenty ninth harmonics are derived to generate the required wave forms, consisting of the sum of these harmonics, are within a field from 10 mHz to 10 Hz.

One fundamental frequency particularly beneficial to the user is 1.56 Hz.

According to the invention, the adder circuit consists of a microprocessor with backing memory designed to receive command signals from a special communications interface enabling the user to programme operation of the electromagnetic wave generator.

The generator is preferably housed in a suitable container together with an appropriate power supply.

The means of emission consist of at least one air solenoid, although numerous alternatives are possible, including combinations of a number of different means of emission as described below.

Tests carried out in university research laboratories show that the magnetic field on the surface of the container housing the generator of electromagnetic waves for medical use for personal physical and psychological wellbeing is between 15 and 18 microTesla, decreasing rapidly to 0.2 microTesla at a distance of 20 cm from the generator.

These values of magnetic field are well below the maximum acceptable levels (100 microTesla) specified in current legislation on exposure to electrical and magnetic fields in domestic and external environments.

The generator is able to emit variable frequency electromagnetic waves over a wide spectrum, including components with periods of between 6 milliseconds and 2 seconds.

The generator of electromagnetic waves for medical use for personal physical and psychological wellbeing also incorporates a timer to deactivate it after a predetermined period of continuous operation, for example, after thirty minutes.

The state of wellbeing caused by the generator is supported by physical-biological analyses.

In fact, interaction between low intensity magnetic fields induced by modest electrical fields and cellular structures in general influences the metabolism and, in particular, the interstitial fluids and biological membranes. The electromagnetic radiation emitted by the generator modulates thermodynamic kinetics, particularly in the case of weak molecular bonds.

The low frequency components of the waves emitted, being in harmony with the vibrations of the cellular structures themselves, produce micro-resonance, allowing a state of natural physiological equilibrium to be achieved rapidly.

At the same time, the medium frequency components of the waves emitted accentuate the mobility of ionic and polar species in the interstitial fluid, thus reducing the energy requirement of membranes normally responsible for the continuous movement of fluid from cell to cell.

The high frequency components of the waves emitted amplify the previously described effects, generally accelerating achievement of physiological and chemical equilibrium and metabolic exchange in the cells.

The general sensation of subjective wellbeing obtainable from exposure to the waves emitted by the generator is comparable with that produced by exposure to temperate solar radiation.

DESCRIPTION OF THE DRAWINGS

Other features and advantages of the invention will become evident on reading the following description of one embodiment of the invention, given as a non-binding example, with the help of the enclosed drawings, in which.

DESCRIPTION OF ONE EMBODIMENT

In the figures, the reference number 10 generally indicates an electromagnetic wave generator, in this specific case, a generator of electromagnetic waves for medical use for personal physical and psychological wellbeing.

Figure 1:
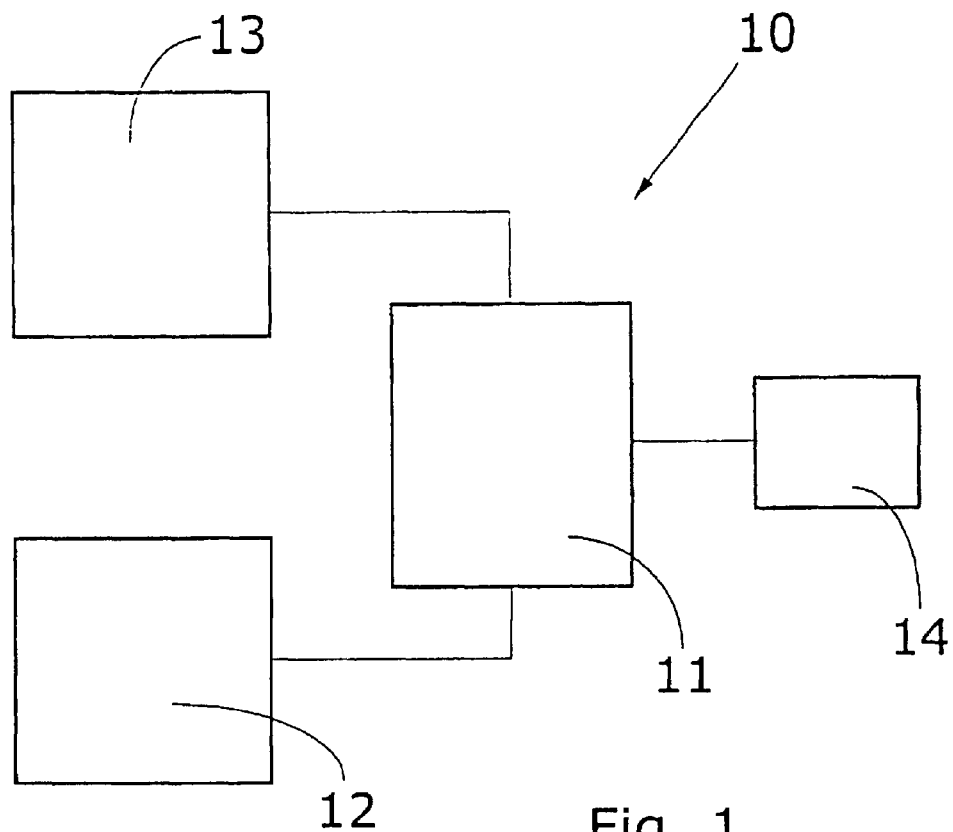
FIG. 1 represents a block diagram of a generator according to the invention.

With reference to the block diagram in FIG. 1, it can be seen that the generator 10 has programmable control means consisting of, for example, at least one microprocessor 11 with backing memory designed to control the means of wave form generation, consisting of, for example, an oscillating circuit 12.

The microprocessor 11 can be activated via a switch or button 13 and is designed to control stability of the oscillating circuit 12 and transmit the respective signals to the means of emission 14.

In accordance with one embodiment, the microprocessor sets the basic frequency of the oscillating circuit 12 which generates the fifth, ninth, thirteenth, seventeenth, twenty first, twenty fifth and twenty ninth order harmonics with respect to the above basic frequency, normally in a field of between 10 mHz and 10 Hz.

Once the stability of the generated harmonics has been verified, the microprocessor 11 transmits the sum of those harmonics to the means of emission 14 which transmit the generated wave form into the environment for a predetermined period of time and at a predetermined intensity.

The fundamental steps of this procedure are then repeated a number of times.

The microprocessor 11 can thus be programmed in such a way as to command the oscillating circuit 12 to generate harmonics based on a number of basic frequencies.

Tests carried out by the applicant have shown that the best results can be obtained using the following frequencies as the initial fundamental frequencies for generating the harmonics: 5.75, 4.10, 2.95, 1.65, 1.57, 0.4, 0.39, 0.166, 0.140, 0.014 Hz.

Figure 2:
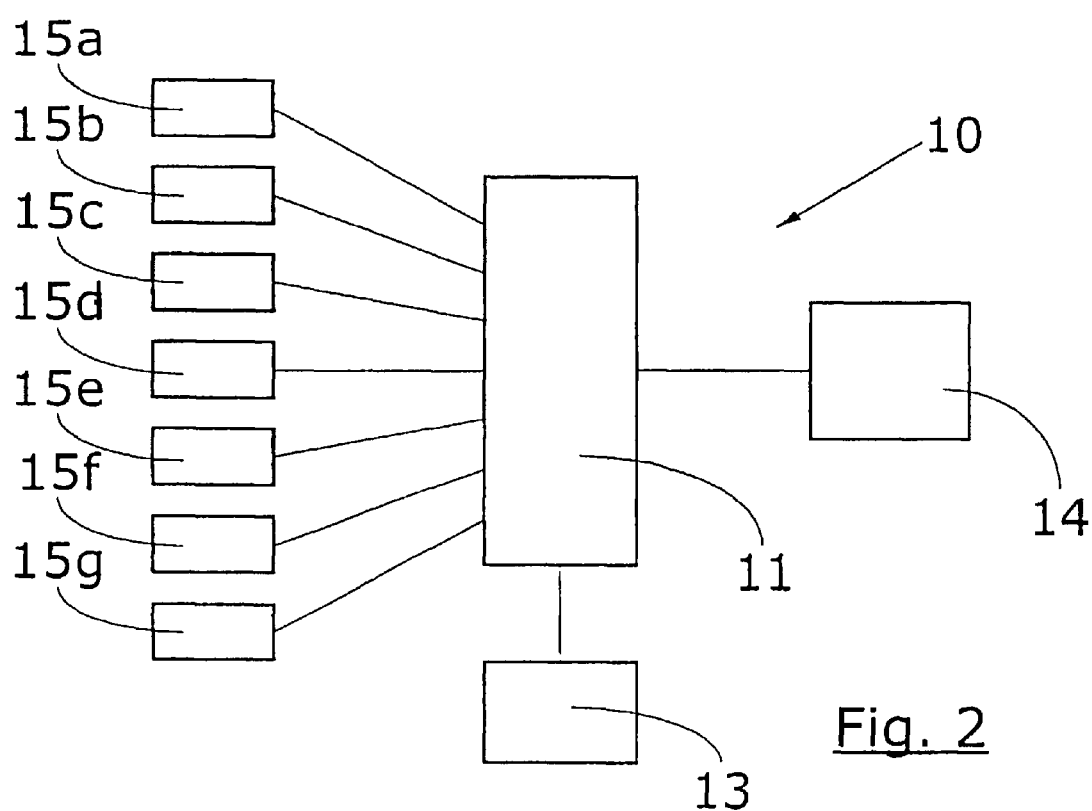
FIG. 2 represents a block diagram of a generator with a number of oscillating circuits.

FIG. 2 illustrates another embodiment incorporating a number of wave generators 15a, 15b, 15c, 15d, 15e, 15f, 15g. In this case they are again connected to the microprocessor 11 and designed, respectively, to emit the fifth, ninth, thirteenth, seventeenth, twenty first, twenty fifth and twenty ninth harmonics of the basic frequency.

The microprocessor 11 is designed to add and mix the waves coming from generators 15a, 15b, 15c, 15d, 15e, 15f, 15g and transmit the result to the means of emission 14.

Figure 3:
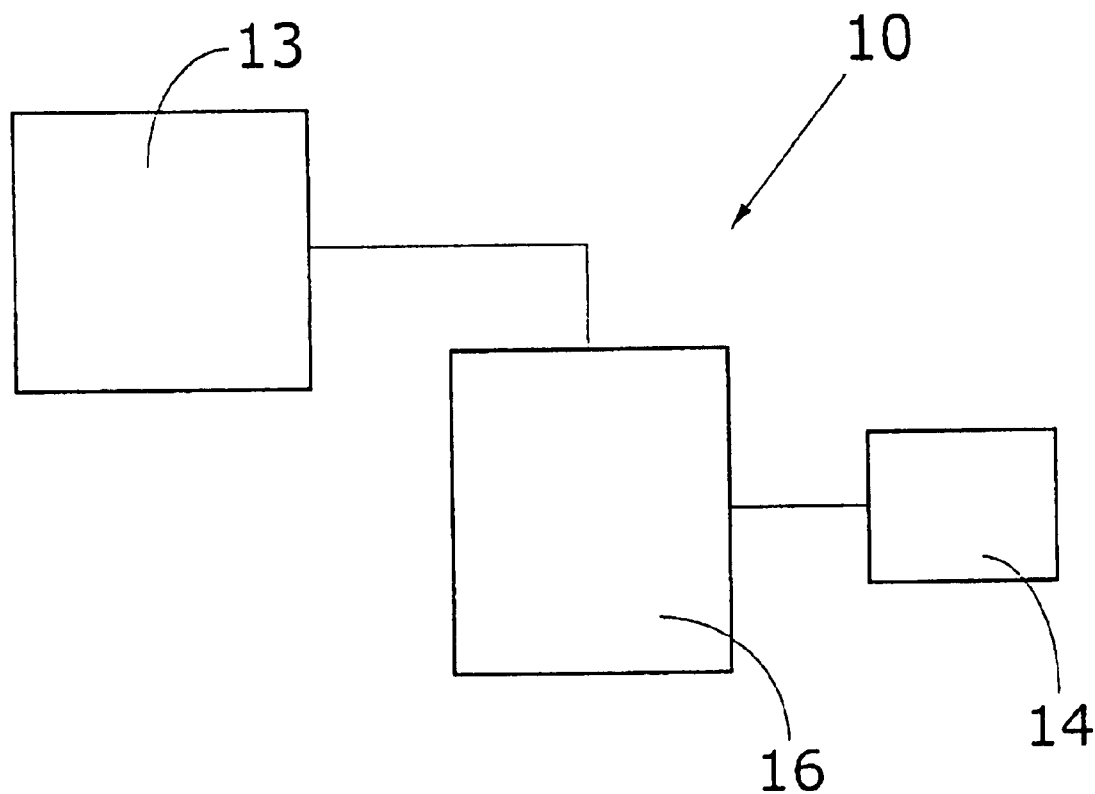
FIG. 3 represents a generator according to a different embodiment.

FIG. 3 illustrates an embodiment with a microprocessor 16 which incorporates the wave form means of generation and which is therefore indistinguishable from the latter.

The microprocessor 16 contains a number of predetermined samples of a wave generated by a respective number of multiple harmonics of a pre-determined fundamental frequency.

Figure 4:
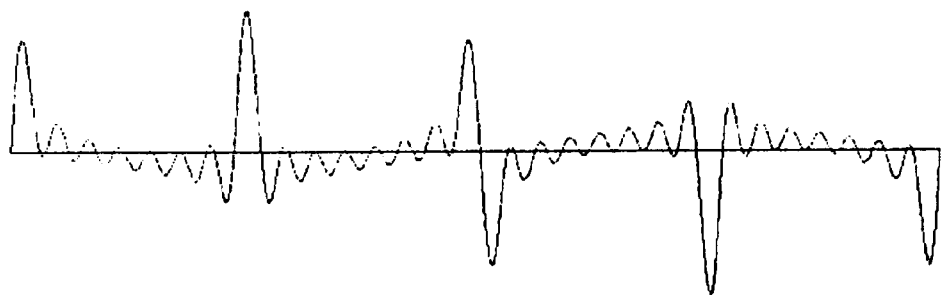
FIG. 4 represents the pattern of an electromagnetic wave over a period of time.

These samples may be selected to enable the wave form of interest to be reconstructed as faithfully as possible (FIG. 4).

Although the preferred field for the basic frequency is between 10 mHz and 10 Hz, the invention is also able to operate with a much more extensive range of basic frequencies, in particular, infrasonic and ultrasonic.

The means of emission 14 may consist of at last one air solenoid, or a modulable infrared emitter, or a modulable ultraviolet emitter, or a very low or very high frequency loudspeaker, or an electrostatic field generator.

The type of emission means is clearly determined by the basic frequency selected and the hypothetical features of the environment where the generator 10 is to be used.

In all the embodiments illustrated above, the generator of electromagnetic waves for medical use 10 is powered by an appropriate source of energy, for example a commercially available replaceable battery.

The entire generator 10 can be housed in a relatively small watertight container, measuring just a few dozen cubic centimeters.

The generator of electromagnetic waves for medical use functions as described below.

Pressing the button or switch 13 powers the respective microprocessor 11 which commands and regulates generation of the electromagnetic waves produced by oscillating circuits 12 or 15a, 15b, 15c, 15d, 15e, 15f, 15g.

The microprocessor 16 reconstructs the signals by means of the samples, automatically regulating amplitude in relation to the value of each respective frequency.

In each case, the wave train is mixed by the microprocessor 11 or 16 and transmitted to the means of emission 14 which radiate the electromagnetic waves into the external environment where the users consequently perceive a sense of general wellbeing and a positive attitude.

In addition, the generator 10 may be equipped with a special communications interface (not shown in the drawings) for user programming.

It is therefore possible to determine, for various applications, the basic frequency for generation of the harmonics, the period and intensity of emission of each wave form generated and the time sequence of wave form emission.

The electromagnetic wave generator 10 may also be equipped with a timer to deactivate it after a predetermined period of continuous operation, for example, after thirty minutes.

The invention is described above with reference to certain particular forms of embodiment.

However, it is clear that the invention may be modified and varied in numerous ways which fall within its objectives in the context of technical equivalencies.

What is claimed is:

1. A generator (10) of electromagnetic waves for medical use for personal physical and psychological well being, comprising means for generating a succession of electromagnetic waves oscillating at predetermined fundamental frequencies, wherein said fundamental frequencies range between 10 mHz and 10 Hz, and in that said generator further comprises:

at least one oscillating circuit (12; 15a–15g) to generate one or more wave harmonics starting from one or more of said fundamental frequencies;

control means for mixing the said waves; and means (14) for emitting the waves into a room which can be occupied by one or more users, whereby each wave generated by mixing of said waves is constituted by the sum of a series of harmonics of fifth, ninth, thirteenth, seventeenth, twenty-first, twenty-fifth and twenty-ninth order in respect of said respective fundamental frequencies.

2. A generator (10) according to claim 1, wherein said control means for mixing said waves consist of a summation circuit that mixes the harmonic waves and generates a resulting wave form to be emitted into the environment surrounding the generator for a pre-determined period of time at a predetermined intensity.

3. A generator (10) according to claim 2, wherein said summation circuit is a microprocessor (11, 16) with backing memory receiving command signals by a suitable communications interface enabling an user to program said microprocessor.

4. A generator (10) according to claim 3 wherein microprocessor (16) comprises means for generating wave forms according to a number of predetermined samples.

5. A generator (10) according to claim 1, wherein it is housed inside a possibly watertight container together with an appropriate energy source acting as a power supply.

6. A generator (10) according to claim 5 wherein said energy source consists of a replaceable battery.

7. A generator (10) according to claim 1 wherein said means (14) for emitting the waves consist of at least one air solenoid, or a modulable infrared or ultraviolet emitter, or a very low or very high frequency loudspeaker, or an electrostatic field generator.

8. A generator (10) according to claim 1, wherein it comprises a plurality of said emitting means (14) in combination.

9. A generator (10) according to claim 1, wherein said fundamental frequencies for generating the harmonic waves have values of 5.75, 4.10, 2.95, 1.65, 1.57, 0.4, 0.39, 0.166, 0.140, 0.014 Hz respectively.

10. A generator (10) according to claim 1, wherein it comprises a suitable interface for connection to a computer for programming the generator itself, in terms of the time sequence, frequency and intensity of the electromagnetic waves to be emitted.

* * * * *